(12) United States Patent
Yang et al.

(10) Patent No.: US 7,611,508 B2
(45) Date of Patent: Nov. 3, 2009

(54) FLOATING SLEEVE MICROWAVE ANTENNA FOR TUMOR ABLATION

(75) Inventors: Deshan Yang, Madison, WI (US); John Michael Bertram, Fridley, MN (US); Mark Christopher Converse, Cottage Grove, WI (US); John Goodwin Webster, Madison, WI (US); David Mahvi, Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 437 days.

(21) Appl. No.: 11/210,063

(22) Filed: Aug. 23, 2005

(65) Prior Publication Data
US 2007/0049917 A1 Mar. 1, 2007

(51) Int. Cl.
*A61B 18/18* (2006.01)
*A61F 2/00* (2006.01)
*A61N 1/00* (2006.01)

(52) U.S. Cl. .................... 606/33; 607/101; 607/156

(58) Field of Classification Search ............. 606/32–35, 606/41, 48–50; 607/101, 102, 154, 156
See application file for complete search history.

(56) References Cited

U.S. PATENT DOCUMENTS

| | | | | |
|---|---|---|---|---|
| 4,700,716 A | * | 10/1987 | Kasevich et al. | ............ 607/156 |
| 5,358,515 A | * | 10/1994 | Hurter et al. | ................ 607/101 |
| 5,405,346 A | * | 4/1995 | Grundy et al. | ................ 606/41 |
| 5,971,983 A | * | 10/1999 | Lesh | ............................ 606/41 |
| 6,245,062 B1 | * | 6/2001 | Berube et al. | ................. 606/33 |
| 6,289,249 B1 | * | 9/2001 | Arndt et al. | ................. 607/101 |
| 6,325,796 B1 | * | 12/2001 | Berube et al. | ................. 606/33 |

OTHER PUBLICATIONS

Koichi Ito et al, Interstitial Applicator Composed of Coaxial Ring Slots for Microwave Hyperthermia, Proceedings of ISAP, Chiba, Japan, 1989.*
Christopher L. Brace et al., Analysis and experimental validation of a triaxial antenna for microwave tumor ablation, 2004 IEEE MTT-S Digest, Madison, Wisconsin.
Koichi Ito et al., Interstitial Applicator Comosed of Coaxial Ring Slots for Microwave Hyperthermia, Proceedings of ISAP '89, Chiba, Japan, 1989.
Christopher, L. Brace et al., Microwave Ablation With a Triaxial Antenna: Results in ex vivo Bovine Liver, IEEE Transactions on Microwave Theory and Techniques, vol. 53, No. 1, Jan. 2005.
Takashige Terakawa et al., Design of Interstitial Ring-Slot Application for Microwave Hyperthermia, IEEE Engineering in Medicine & Biology Society 11th Annual International Conference, 1989 Chiba-Shi, Japan.
Koichi Ito et al., Thin Application Having Coaxial Ring Slots for Interstitial Microwave Hyperthermia, 1990 IEEE, Chiba, Japan.
PCT International Search Report for PCT Application No. US06/32908, dated Jan. 24, 2008, ISA/US.

* cited by examiner

*Primary Examiner*—Michael Peffley
(74) *Attorney, Agent, or Firm*—Boyle Fredrickson, S.C.

(57) ABSTRACT

An antenna for microwave tumor ablation provides coaxial antenna conductors surrounded by an insulated sleeve of length and size promoting destructive interference of axial microwave energy passing inside and outside of the sleeve to limit the tail of SAR power toward the skin.

16 Claims, 2 Drawing Sheets

FLOATING SLEEVE MICROWAVE ANTENNA FOR TUMOR ABLATION

STATEMENT REGARDING FEDERALLY SPONSORED RESEARCH OR DEVELOPMENT

This invention was made with United States government support awarded by the following agency: NIH DK058839. The United States has certain rights in this invention.

CROSS-REFERENCE TO RELATED APPLICATIONS

--

BACKGROUND OF THE INVENTION

The present invention relates to microwave probes for tissue ablation and in particular to a microwave antenna providing improved localization during tissue heating.

Microwave ablation may be used to treat tumors, for example in the liver, in patients who are not eligible for surgical removal of the tumor. In such microwave ablation, a coaxial microwave antenna is inserted into the tissue to the point of the tumor to conduct microwave energy to that location. Tissue ablation is caused by depositing energy in the region surrounding the antenna and its conversion to heat. Energy deposited into the tissue is often characterized by the Specific Absorption Rate (SAR). The SAR pattern, and thus the size and shape of the ablation region, is a function of the microwave power, the duration of the application of power, and the design of the antenna. Microwave ablation does not require a separate ground pad attached to the patient, and thus may be distinguished from ablation at lower frequencies.

Currently, microwave ablation can effectively treat tumors only less than about two centimeters in diameter. This is because microwave power to the antenna must be limited to prevent excessive heating along a "tail" away from the tumor and along the length of the antenna. During percutaneous treatment, this tail of heating may damage healthy tissue and burn the skin.

This heating in the tail along the antenna results from a number of effects including the SAR pattern of the antenna, resistive heating of the shield of the coaxial antenna structure, and thermal conduction of heat along the metallic conductors of the antenna from the tumor site. Different types of antennas have been developed to prevent or reduce this heating tail including designs that use gaps and ring structure attached to the center and/or outer antenna conductor to provide capacitive and inductive elements to form resonant traps blocking current flow on the outer conductor.

BRIEF SUMMARY OF THE INVENTION

The present invention suppresses the tail of the SAR pattern by use of a floating sleeve, which creates two paths of microwave propagation along the axis of the antenna from the tumor site to the skin. A dielectric along one path shifts the phase of the microwave energy to destructively interfere with the microwave energy along the second path thus effectively reducing the microwave energy near the distal portion of the antenna. The present invention may be used with other techniques for reducing the heating tail, such as suppressing shield current flow, and thus shield current heating with resonant traps and thermal insulation of the shield from tissue.

Specifically, the present invention provides a microwave ablation antenna having a coaxial antenna with a center conductor and an outer conductor extending along an axis to allow positioning of a proximal end of the coaxial antenna within a patient at a site of the tumor, and the distal end of the coaxial antenna outside of a patient to be connected to a microwave source having a microwave frequency. A sleeve is positioned outside of, and electrically insulated from, the outer conductor, and the sleeve extends along the axis to provide a relative phase shift between microwave energy traveling axially outside the outer conductor and within the sleeve, and microwave energy traveling axially outside the sleeve, where the relative phase shift is substantially an odd, multiple of pi radians.

It is thus an object of the invention to use destructive interference to shape the SAR pattern, concentrating the SAR pattern at the proximal tip and away from the distal end of the antenna.

The microwave frequency may be at least 500 megahertz.

It is thus another object of the invention to provide an antenna structure suitable for high frequency microwave ablation.

The sleeve may be metal and separated from the outer conductor with an insulator.

Thus it is another object of the invention to provide a simple structure allowing an arbitrary control of wavelength through the selection of insulator properties. It is another object of the invention to provide a simple structure that does not require electrical connection to the other coaxial conductors.

This sleeve may be a continuous coaxial tube.

Thus it is another object of the invention to provide axially symmetric different paths of energy flow.

The antenna may further include an insulator outside of the sleeve.

It is thus another object of the invention to provide a biocompatible outer antenna material. It is a further object of the invention to provide an insulation layer from the antenna that may reduce tissue heating from conductor heating.

The sleeve is sized to be wholly within the patient during use.

It is therefore an object of the invention to ensure destructive cancellation of microwave energy in the distal region of the antenna and thereby minimize damage to normal tissue along the axis of the antenna.

The sleeve may provide a wavelength of microwave energy traveling axially outside of the outer conductor and within the sleeve of at least 5 times the wavelength of microwave energy traveling axially outside of the sleeve. The sleeve may be substantially one-half the wavelength of the microwave energy traveling axially outside the sleeve.

It is thus an object of the invention to minimize the length of the sleeve by maximizing the difference between the wavelengths inside and outside of the sleeve.

The sleeve may be less than 100 millimeters in axial extent.

It is thus another object of the invention to provide an antenna practical for use with relatively shallow tumors.

The sleeve may be free to slide axially with respect to the outer conductor.

It is thus another object of the invention to provide a simple means of adjusting the ablation pattern using a sleeve that is not electrically connected to the other antenna conductors.

The antenna may further include a capacitive and inductive element reducing current flow on the outer conductor.

It is thus another object of the invention to provide a method of directly shaping the SAR pattern that may be combined with methods of suppressing current flow on the outside of the outer coaxial conductor.

A kit of antennas may be produced with sleeves positioned at different distances from the proximal ends of the antennas to provide different ablation volumes.

It is thus another object of the invention to provide a set of antennas that may be selected among to match a particular tumor to be ablated.

These particular objects and advantages may apply to only some embodiments falling within the claims and thus do not define the scope of the invention.

DETAILED DESCRIPTION OF THE PREFERRED EMBODIMENT

Figure 1:
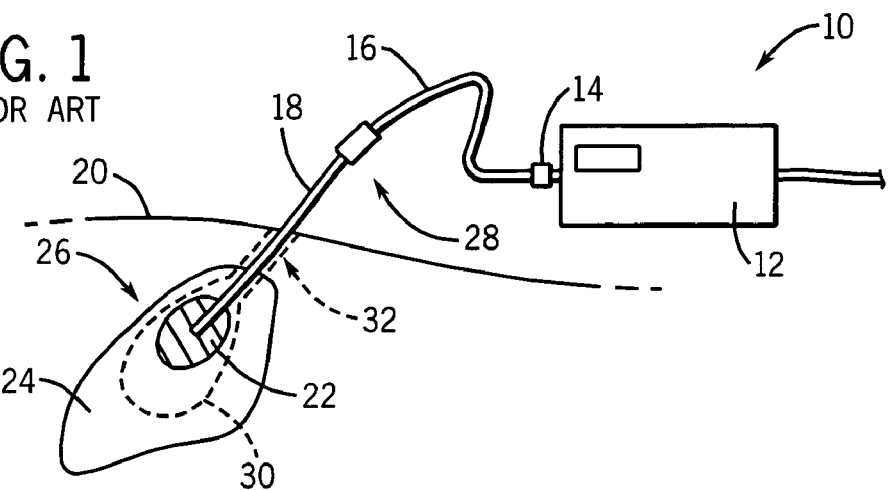
FIG. 1 is a simplified representation of a prior art microwave ablation system showing a microwave source connected to a microwave antenna positioned at the site of the liver tumor and showing the SAR pattern that produces a substantial heating tail at high powers.

Referring now to FIG. 1, a microwave ablation antenna 10 may include a microwave power supply 12 of standard design providing microwave energy at frequencies from 0.5 to 5 gigahertz. The microwave power supply 12 may be connectable through connector 14 to feed line 16. The feed line 16 may be a standard coaxial cable providing a standard impedance (typically 50 ohms) between a center conductor that is surrounded by a dielectric and braided shield, which is in turn covered with an insulating sheath.

The feed line 16 attaches to a microwave antenna 18 sized for percutaneous insertion into a patient 20 to a tumor site 22, for example, within a liver 24. During use, the proximal end 26 of the microwave antenna 18 is placed within the tumor site 22 while a distal end 28 remains outside of the patient to connect to the feed line 16.

Figure 2:
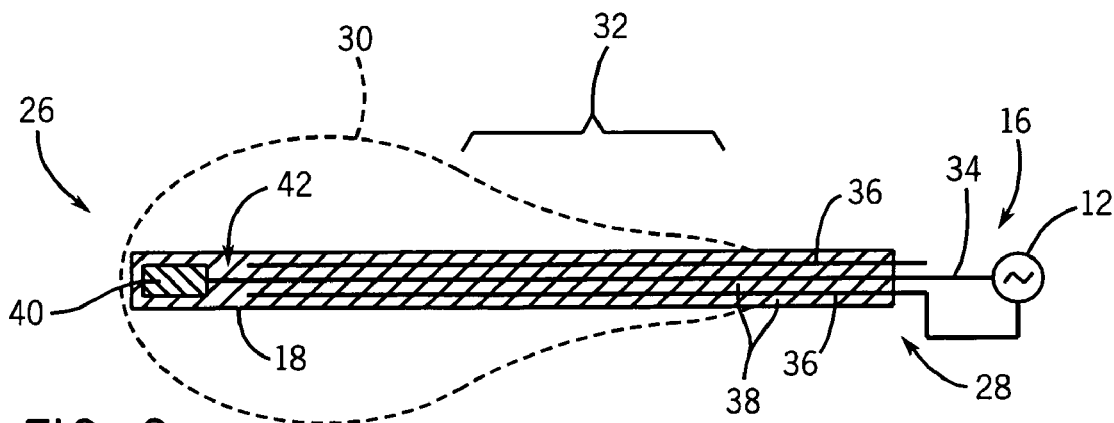
FIG. 2 is an axial cross-section of the antenna of FIG. 1 showing the coaxial inner and outer conductors including a capacitor structure for reducing shield current flow.

As shown in FIG. 2, the microwave power supply 12 through the feed line 16 provides an alternating voltage across a center conductor 34 of the antenna 18 and an outer coaxial conductor 36 (also termed the shield). The space between the conductors 34 and 36 may be filled with a dielectric layer 38 which may be continued outside of the outer coaxial conductor 36 to provide for electrical and thermal insulation of the antenna 18.

The center conductor 34 may terminate at a conductive cylindrical slug 40 providing an effective axial capacitance across a gap 42 to the outer coaxial conductor 36. This design as well as similar capacitor choke designs in which additional structures are attached to the outer coaxial conductor 36 can provide tuned structures reducing current flow on the outside of the outer coaxial conductor 36.

The application of microwave energy to the antenna 18 produces a heating pattern 30 concentrated in the tumor site 22 but having a heating tail 32 leading back to the distal end 28. Generally, for the antenna 18 to accept higher power to ablate larger tumors, the heating tail 32 must be minimized to reduce damage to healthy tissue outside the tumor site 22 and the near the skin.

Figure 3:
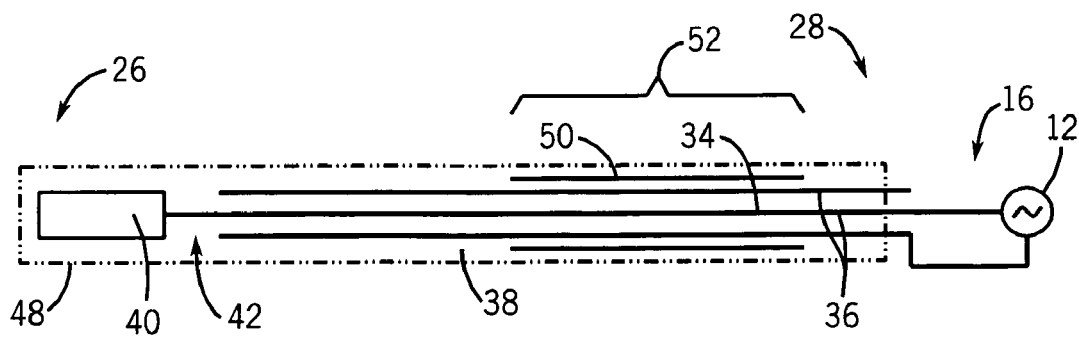
FIG. 3 is a figure similar to that of FIG. 2 showing the addition of a floating sleeve conductor per the present invention.

Referring now to FIG. 3, the present invention provides an antenna 48 that may be used with the standard microwave power supply 12 and feed line 16. The antenna 48 also has an inner conductor 34 and outer coaxial conductor 36, and optionally also has a structure such as a conductive cylindrical slug 40 and gap 42 for shield current suppression, but further includes a floating sleeve 50 electrically insulated from the outer coaxial conductor 36. Generally, the location of the floating sleeve 50 along the axis of the antenna 48 may be freely varied, however, the length 52 of the sleeve must be controlled according to the frequency of the microwave power supply 12 and the relative properties of the sleeve materials and the surrounding tissue. The floating sleeve 50 is positioned so as to not cover gap 42 and to provide the desired dimension of the heating pattern 30 near the proximal end 26 and generally will have a length less than 100 millimeters in axial extent.

Figure 4:
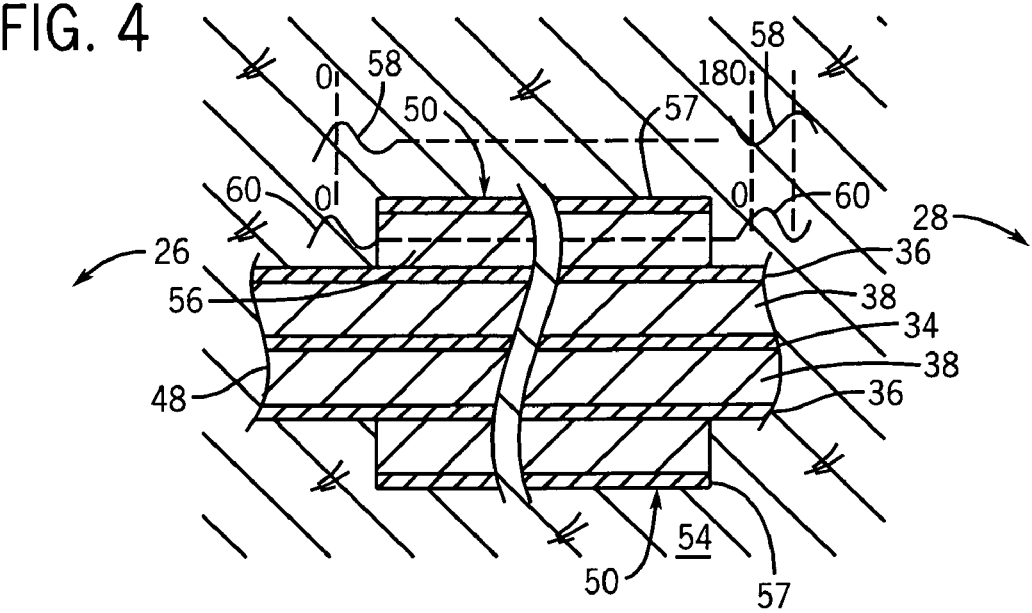
FIG. 4 is an enlarged fragmentary view of a first embodiment of the antenna of FIG. 3 showing two paths of microwave energy inside and outside of the floating sleeve having a metal conductor separating tissue from an insulating layer.

Referring now to FIG. 4 in a first embodiment, the floating sleeve 50 includes an outer conductor 57, for example a metallic tube, separated from the outer coaxial conductor 36 by a dielectric material 56 which need not, but can be, the same material as dielectric layer 38. The dielectric material 56 may be of the same axial length as the outer conductor 57 or longer or shorter subject to the constraints described below. In this simple embodiment, the outer conductor 57 is in direct contact with tissue 54 of the patient as is the coaxial outer conductor 36. In a second embodiment, described below, the outer conductor 57 may be covered with a second dielectric.

While the inventors do not wish to be bound by a particular theory, they believe the present invention works as follows: Microwave energy emanating from the proximal end 26 of the antenna 48 produces a wave front including waves 58 and 60 passing axially from the proximal end 26 of the antenna 48 to the distal end 28. As the wave front arrives at the proximal end of the floating sleeve 50, waves 58 and 60 being part of the same wave front are approximately in phase. Wave 60 enters the dielectric material 56 between the outer coaxial conductor 36 and the floating sleeve 50, which typically has a much smaller relative permittivity than the permittivity of the tissue 54. As a result, the wavelength of the wave 60 is longer, leading to a smaller phase shift of the wave, so that when waves 58 and 60 arrive at the distal end of the floating sleeve 50 they may be out of phase. The axial length of the floating sleeve 50 is set so that the phase difference between waves 58 and 60 is substantially 180 degrees (pi radians) upon exiting the floating sleeve 50 resulting in a destructive cancellation of the electromagnetic energy.

The wavelength of the waves 58 and 60 will be a function of the permittivities of the material through which they travel. In a preferred embodiment, the floating sleeve 50 will be a conductive metal and the dielectric material 56 a material such as Teflon having a permittivity of approximately 2 in contrast to the permittivity of tissue 54 which will typically be more than five times greater, being for example, 43 at 2.45 gigahertz in liver. As such, the wavelength of wave 60 inside the sleeve 50 may be ten times longer than the wavelengths of wave 58 outside the floating sleeve 50, and accordingly, the sleeve length 52 may be acceptably set to one-half the wavelength of the wave 58 outside of the floating sleeve 50 (or an odd multiple). A large difference between permittivities (and thus wavelengths) increases the difference between the phases of the waves 58 and 60 per distance along the axis, thus decreasing the necessary length of the floating sleeve 50. A short length 52 of floating sleeve 50 may be desired to ensure that the floating sleeve 50 remains within the patient so that the region of destructive interference is much below the patient's skin.

Typically the thickness of the dielectric material 56 between the floating sleeve 50 and the outer coaxial conductor 36 should be at least 0.1 millimeter and as much as 0.3 millimeters to admit sufficient energy to provide effective destructive cancellation of wave 58.

Figure 5:
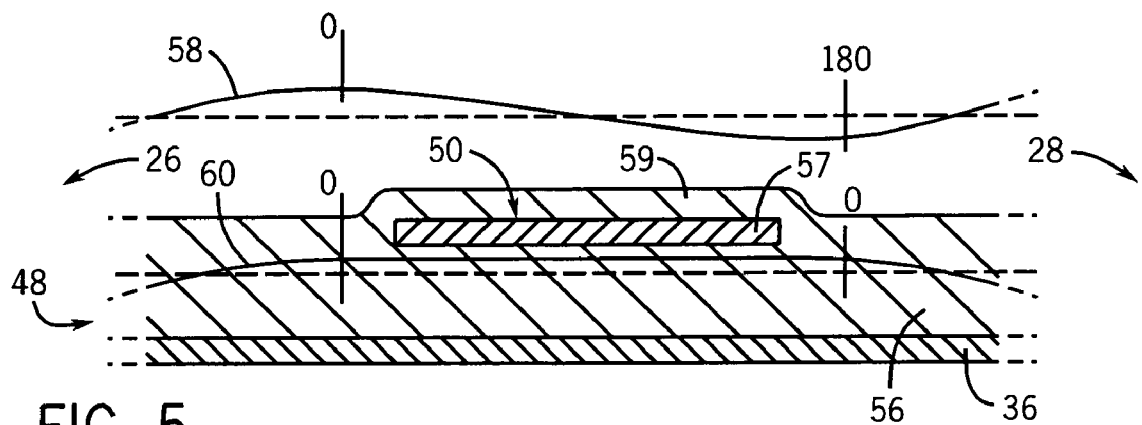
FIG. 5 is a figure similar to that of FIG. 4 showing an alternative embodiment having an insulating covering outside of the metal conductor and adjusted for minimal sleeve length.

Referring now to FIG. 5 in a second embodiment, the floating sleeve 50 will be covered by an insulating layer 59, for example, also Teflon, as will the outside of outer coaxial conductor 36. This insulating layer 59 outside of floating sleeve 50, having a lower permittivity than tissue 54, effectively increases the average wavelength of the wave 58 over that of the embodiment of FIG. 4. This increase in wavelength may be accommodated by increasing the length 52 of the floating sleeve 50. Again, a minimum length 52 of floating sleeve 50 is obtained when the length 52 of the sleeve is equal to one-half of the wavelength of wave 58.

Figure 6:
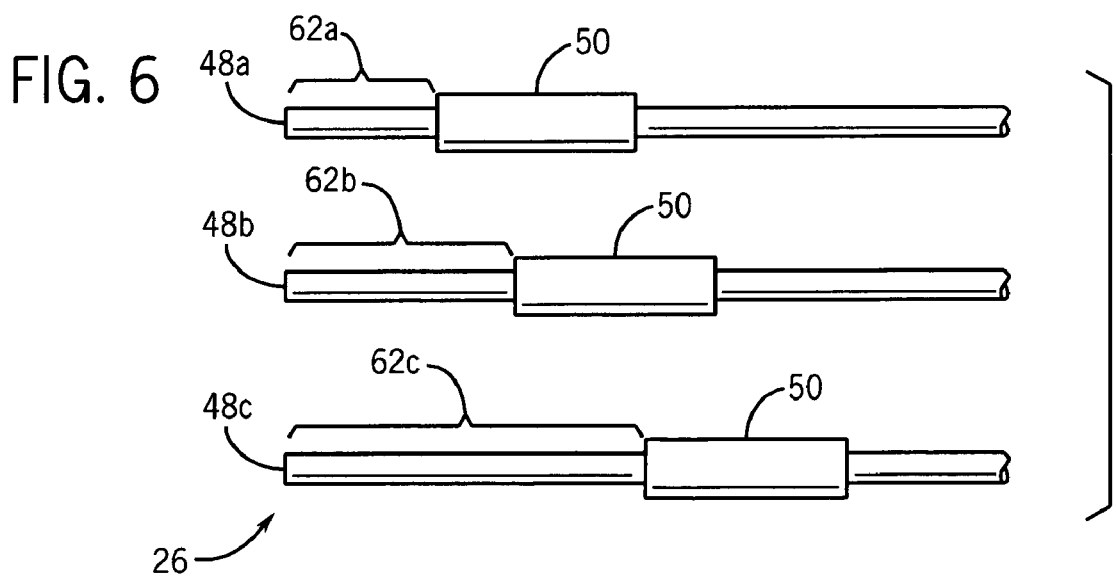
FIG. 6 is a side view of the distal ends of three antennas providing for different shield locations to control the effective volume of the SAR pattern.

Referring now to FIG. 6, the independence of the mechanism of destructive cancellation provided by the floating sleeve 50 from the electrical elements of the outer coaxial conductor 36 and center conductor 34 (not shown in FIG. 6) allow the floating sleeve 50 to be easily repositioned. In this way, a number of different antennas 48a through 48c may be created where the distance 62a through 62c between the proximal ends of the sleeves 50 and the proximal ends 26 of the antennas 48 is varied so as to change the effective size of the heating pattern 30. Sleeves 50 may slide axially over the outer coaxial conductor 36 (for example, as shown in FIG. 4) with sufficient friction to be held in place during use, or may be manufactured with different fixed distances 62 and held in place with an outer insulating coating. The distances 62 may be limited to convenient sizes, for example, of one-half centimeter or one centimeter increments.

Example

An antenna 48 constructed according to the above-described principles may be based on 50 ohm UT-085 semirigid coaxial cable wrapped with a thin layer of Teflon tape. Generally, the impedance of the antenna is set to be substantially equal to the impedance of the feed line of approximately 50 ohms. The floating sleeve 50 may be made of a section of copper tubing having a 3.2 millimeter outer diameter and a 2.5 millimeter inner diameter and approximately 19 mm in length having a proximal end about 22 mm from the proximal tip of the antenna. The whole assembly may then be rewrapped in Teflon tape and heat shrunk to the coaxial cable. The overall radius of the antenna is relatively small and suitable for intraoperative percutaneous therapies. The power supply may, for example, be a 300-watt power supply operating at 2.45 GHz.

It is specifically intended that the present invention not be limited to the embodiments and illustrations contained herein, but include modified forms of those embodiments including portions of the embodiments and combinations of elements of different embodiments as come within the scope of the following claims.

We claim:
1. A microwave ablation antenna comprising:
a substantially non-helical coaxial antenna having a center conductor and an outer conductor extending along an axis to allow positioning of a proximal end of the coaxial antenna within a patient at a site of a tumor and a distal end of the coaxial antenna outside of a patient to be connected to a microwave source having a microwave frequency; and
a sleeve outside and electrically insulated from the outer conductor and the center conductor, the sleeve extending along the axis to provide a relative phase shift between microwave energy traveling axially outside the outer conductor and within the sleeve, and microwave energy traveling axially outside the sleeve, the relative phase shift equal substantially to an odd multiple of one half a wavelength of the microwave frequency;
whereby microwave energy distal to the sleeve is suppressed by destructive cancellation of the microwave energy at an exit of the sleeve.

2. The microwave ablation antenna of claim 1 wherein the microwave frequency is at least 500 megahertz.

3. The microwave ablation antenna of claim 1 wherein the sleeve is metal and separated from the outer conductor with an insulator.

4. The microwave ablation antenna of claim 1 wherein the sleeve is a continuous coaxial tube.

5. The microwave ablation antenna of claim 1 further including an insulator outside of the sleeve.

6. The microwave ablation antenna of claim 1 wherein the sleeve is sized to be wholly within the patient during use.

7. The microwave ablation antenna of claim 1 wherein the sleeve provides a wavelength of microwave energy traveling axially outside the outer conductor and within the sleeve of at least five times the wavelength of the microwave energy traveling axially outside the sleeve.

8. The microwave ablation antenna of claim 7 wherein the sleeve is substantially one half the wavelength of the microwave energy traveling axially outside the sleeve.

9. The microwave ablation antenna of claim 1 wherein the sleeve includes an insulator having a dielectric of at least five times less than the dielectric of tissue of the patient.

10. The microwave ablation antenna of claim 1 wherein the sleeve is less than 100 mm in axial extent.

11. The microwave ablation antenna of claim 1 wherein the sleeve may slide axially with respect to the outer conductor.

12. The microwave ablation antenna of claim 1 further including a microwave source having a frequency in a range from 0.5 to 5 GHz.

13. The microwave ablation antenna of claim 1 further including at least one of a capacitive and inductive element reducing current flow on the outer conductor.

14. The microwave ablation antenna of claim 1 wherein the sleeve has an electrical length equal substantially to an odd multiple of the microwave energy traveling outside the sleeve and substantially unequal to an odd multiple of the microwave energy traveling within the sleeve.

15. A method of treating a tumor comprising the steps of:
(a) positioning a substantially non-helical coaxial antenna having a center conductor and an outer conductor extending along an axis with a proximal end of the coaxial antenna within a patient at a site of a tumor and a distal end of the coaxial antenna outside the patient; and
(b) connecting the coaxial antenna to a microwave source having a microwave frequency;

wherein the coaxial antenna includes a sleeve outside and electrically insulated from the outer conductor and the center conductor, the sleeve extending along the axis to provide a phase shift between microwave energy traveling axially outside the outer conductor and within the sleeve, and microwave energy traveling axially outside the sleeve of substantially an odd multiple of pi radians so as to cause destructive cancellation of the microwave energy at an axial exit of the sleeve between the energy traveling axially within the sleeve and energy traveling axially outside the sleeve.

16. The method of claim 15 wherein the sleeve has an electrical length equal substantially to an odd multiple of the microwave energy traveling outside the sleeve and substantially unequal to an odd multiple of the microwave energy traveling within the sleeve.

* * * * *